(12) United States Patent
Hirshberg et al.

(10) Patent No.: US 8,287,705 B2
(45) Date of Patent: Oct. 16, 2012

(54) TEMPERATURE COMPENSATION FOR ION-SELECTIVE ELECTRODES

(75) Inventors: Moshe Hirshberg, Brookline, MA (US); Xiaowen Wen, Lexington, MA (US); Hyoungsik Yim, North Chelmsford, MA (US); Dawood Bhaijee, Burlington, MA (US)

(73) Assignee: Thermo Fisher Scientific, Inc., Beverly, MA (US)

( * ) Notice: Subject to any disclaimer, the term of this patent is extended or adjusted under 35 U.S.C. 154(b) by 200 days.

(21) Appl. No.: 12/692,740

(22) Filed: Jan. 25, 2010

(65) Prior Publication Data

US 2011/0180406 A1 Jul. 28, 2011

(51) Int. Cl.
*G01N 27/333* (2006.01)
(52) U.S. Cl. ......... 204/416; 204/419; 204/435; 374/142
(58) Field of Classification Search .................. 204/416, 204/419, 420, 433, 435; 205/787.5, 789, 205/789.5; 374/142, 185
See application file for complete search history.

(56) References Cited

U.S. PATENT DOCUMENTS

| 4,008,141 A | * | 2/1977 | Kotani et al. | 204/420 |
| 4,414,093 A | * | 11/1983 | Redey et al. | 204/412 |
| 5,367,282 A | * | 11/1994 | Clem | 338/22 R |
| 2004/0071190 A1 | * | 4/2004 | Chang | 374/185 |

* cited by examiner

*Primary Examiner* — Kaj K Olsen
(74) *Attorney, Agent, or Firm* — Cesari and McKenna, LLP

(57) ABSTRACT

Temperature compensation for ion-selective electrodes is obtained by positioning a temperature-measuring element in a chamber of limited thermal mass which is in thermal contact with the measuring electrode filling solution but is thermally isolated from other filling solutions in the electrode. In a preferred embodiment, the temperature-measuring element comprises a thermistor enclosed within thin flexible tubing; the electrical leads of the thermistor are forced against a segment of the inner wall of the tubing by an elongated strand of material abutting the thermistor to enhance heat transfer with the thermistor.

16 Claims, 2 Drawing Sheets

TEMPERATURE COMPENSATION FOR ION-SELECTIVE ELECTRODES

BACKGROUND OF THE INVENTION

1. Field of the Invention

The invention relates to temperature compensation for ion-selective electrodes, and is particularly applicable to combination electrodes for potentiometric measurements.

2. Background Information

Ion-selective electrodes are commonly used to measure the activity or concentration of ions in solution. Combination electrodes combine both a measuring electrode and a reference electrode in one body. One very popular form of ion-selective electrode contains filling solutions to provide electrical contact between the solution being measured (the analyte) and the electrodes, as well as to provide a stable reference potential for potentiometric measurements.

When an electrode is immersed in an analyte sample, differences in temperature between the analyte sample and the standard solutions used in calibration can cause significant measurement errors unless temperature compensation is taken into account. In order to achieve fast and accurate measurements, it is necessary to measure the temperature of the sample in a fast and accurate manner so that the effect from temperature change can be corrected. Therefore, it is desirable to have a fast thermal equilibrium between sample solution and thermistor in the probe. The time to reach equilibrium ("the response time for temperature measurement") thus limits one's ability to make a series of rapid measurements on different analytes.

Generally it is desirable to incorporate the temperature sensing element within the electrode itself. One approach incorporates a temperature-sensing element such as a thermistor in the internal filling solution of the working or measuring electrode. See U.S. Pat. No. 7,290,434 B2, issued Nov. 6, 2007 to Jurgen Ammann et al. and assigned to Mettler-Toledo AG. However, some filling solutions are corrosive, and thus the temperature sensing element can be exposed to chemical attack. Additionally, some solutions often impose rigid sealing requirements, which may make inclusion of temperature-sensing elements in them difficult. Thus, while in theory immersion of the temperature sensing element in the measuring filling solution is desirable, practical considerations may militate against this.

Combination electrodes in which the temperature sensing element is incorporated in the reference electrode are also known. See, e.g., certain of the pH electrodes offered by the Schott Instruments Co. However, the large thermal mass presented by the reference filling solution limits the response-time of the temperature sensing element; additionally, temperature gradients caused by diffusion of heat through the reference solution can lead to errors in the indicated temperature and thus errors in the calculated ion concentration.

SUMMARY OF THE INVENTION

Accordingly, it is an object of the invention to provide improved temperature compensation for ion-selective electrode.

Further, it is an object of the invention to provide improved temperature-compensation for ion-selective combination electrodes.

Still a further object of the invention is to provide an improved temperature-compensated ion-selective electrode which rapidly and accurately measures the temperature of an analyte without requiring immersion of temperature sensors in the measuring electrode filling solution.

In accordance with one aspect of the present invention, we provide temperature-compensation for ion-selective electrodes, particularly combination electrodes, that provides good accuracy, good response time, and does not require exposure of the temperature-measuring element to corrosive filling solutions in the measuring electrode.

Electrodes of the combination type typically comprise an inner measuring is electrode surrounded by an outer reference electrode for making potentiometric measurements. The measuring electrode may advantageously be, but is not restricted to, one that uses a corrosive filling solution. An example of such an electrode is one that uses an iodide/triiodide filling solution such as is sold by the Thermo-Orion Corporation under the trademark Ross® electrode.

Within the outer reference electrode, and surrounding the inner measuring electrode in the vicinity of the sensing element of the measuring electrode, we form a temperature-measurement chamber of small thermal mass. This may advantageously be accomplished by sealing off a portion of the reference solution chamber by means of an insulating bung that thermally insulates the chamber from the main mass of the outer electrode filling solution and effectively forms a separate temperature measurement chamber. The temperature-measurement chamber advantageously has a volume less than 10-15% of the main reference chamber, preferably much less, e.g., less than 5%. In one embodiment, the temperature-measurement chamber had a volume of 0.2 milliliters as compared to a volume of 10 milliliters for the main reference chamber. A retaining sleeve encompassing the inner electrode may be positioned on top of the insulating bung to secure the bung in place. The temperature-measurement chamber is filled with a liquid that may be, but need not necessarily be, the same as the outer electrode filling solution; the liquid should have good thermal conductivity.

Positioned within the temperature-measurement chamber is a temperature-sensing element, such as a thermistor. The thermistor is enclosed within a flexible thin-walled sleeve of a thin plastic material such as Teflon® tubing of inner diameter comparable to that of the thermistor. The thermistor may advantageously be fixed in place by heat is shrinking the tubing in the vicinity of the thermistor to hold it securely. It may additionally (or alternatively) be held in place by flexible strands butted against it within the tubing. (As used herein, the term "strand" refers to a thin, elongated segment of material.)

In one embodiment of the invention, the thermistor is secured in place by one or more flexible strands of diameter comparable to that of the inner diameter of the tubing and butted against one or both ends of the thermistor. These strands may serve several purposes. First, they exclude air in the tubing from the immediate vicinity of the thermistor. Air is a good insulator, and its presence would degrade the response time of the thermistor. Second, they may assist in conducting heat to the thermistor in order to improve its response time.

In particular, the lead wires of a thermistor conduct electrical signals from the thermistor to a measuring instrument. They also conduct heat to and from the thermistor. Use is made of this fact in the present invention by butting a flexible strand, having a comparable cross-section to that of the tubing bore, against the end of the thermistor to which the lead wires are connected. The strand pushes the lead wires against, and partially into, the resilient walls of the tubing along that section of tubing coextensive with the strand. Thus, along that section, the thermistor lead wires are separated from the liquid environment in which the tubing is immersed only by the thin wall of the tubing, and enhanced heat transfer can take place between the lead wires and their environment.

Beyond the strand, however, the lead wires are unconstrained and can return to a more central position in the tubing in which they are enveloped by the air within the tubing. Thus, along this further portion, the heat transfer capability of the lead wires is is significantly reduced. Accordingly, when the tubing, and the lead wires within it, exits the temperature-measurement chamber, the lead wires are at least partially shielded from heat exchange with an environment whose temperature may differ from that of the chamber.

The strands may be of any material, metallic or non-metallic. In a preferred embodiment of the invention, the strand or strands are in the form of a thin, flexible, electrically insulated, thermally conductive metallic wire. One very suitable wire is thin aluminum magnet wire; such a wire has a very thin electrical insulation so that it will not interfere with the electrical signals on the thermistor leads; is flexible; and has good thermal conductivity. In this embodiment, the metallic strands additionally serve to exchange heat with the measuring chamber liquid.

In a preferred embodiment, the tubing extends into the temperature-measurement chamber through a first port in the insulating bung that thermally separates the chamber from the main mass of the outer electrode filling solution; preferably circumscribes the inner measuring electrode near the tip which is immersed in an analyte for measurement; and exits the chamber through a second port in the insulating bung. That section of the tubing containing the thermistor preferably circumscribes the inner measuring electrode near the tip which to be immersed in an analyte for measurement. Preferably, it forms one or more loops around the inner electrode to thereby enhance the transfer of heat between the inner electrode and the temperature-measurement chamber.

Enclosing the thermistor in the tubing not only protects the thermistor and its lead wires from surrounding fluids, but also greatly facilitates handling of the thermistor and its positioning in the temperature-measurement chamber. Once the thermistor is placed is within the tubing, that portion of the tubing containing the thermistor is readily formed into a loop of sufficient diameter to circumscribe the inner electrode and is then anchored into place by extending the opposite ends of the tubing through a wall (specifically, the bung) of the chamber.

In one embodiment of the invention, the tubing was a fluorinated ethylene propylene tubing 0.038 inch diameter and 0.006 inch wall thickness. This material is a relatively good heat conductor; is highly chemically resistant; and has low solvent absorption and low gas and vapor permeability.

BRIEF DESCRIPTION OF THE DRAWINGS

The foregoing and other and further objects and features of the invention will be more readily understood on reference to the following drawings when taken in conjunction with the subject detailed description of the invention. In the drawings.

DETAILED DESCRIPTION OF AN ILLUSTRATIVE EMBODIMENT

The preferred embodiment of present invention will be illustrated and described is in the context of a combination electrode for measuring pH, although it will be understood that the invention is not limited to this type of electrode and is more broadly applicable.

Figure 1:
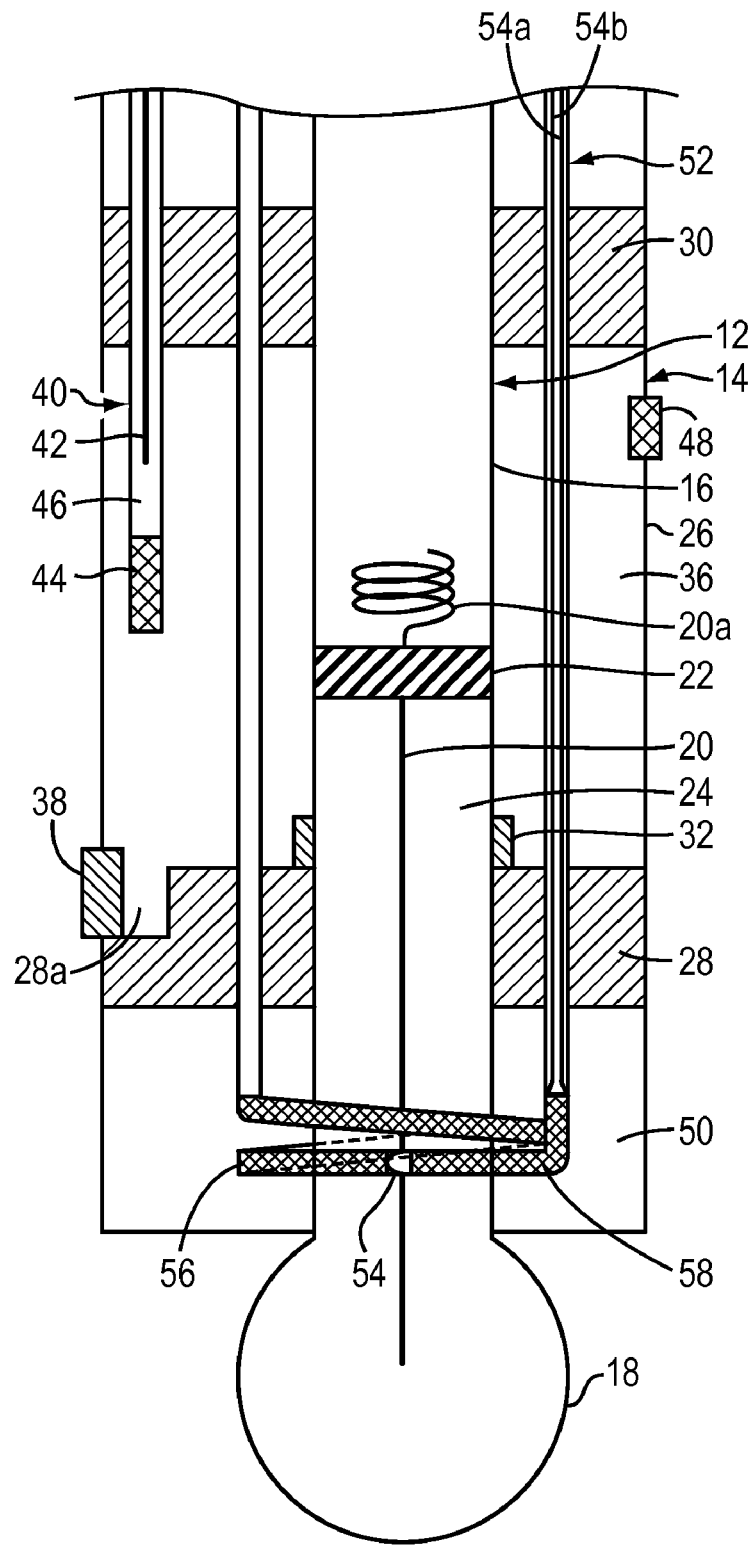
FIG. 1 is a section of a portion of a combination ion-selective electrode in accordance with one embodiment of the invention.

In FIG. 1, a combination electrode has an inner measuring electrode 12 and an outer reference electrode 14 generally surrounding it. The inner electrode has the form of an elongated tube 16 terminating in a rounded bulb 18 comprising a pH sensitive membrane, typically of glass. A conductive electrode 20 (e.g., a platinum wire) extends upwardly through the tube 16 and through a seal 22; it terminates in a coil 20a. During a measurement of the pH of a solution, the coil 20a is connected to one terminal of a high-impedance voltmeter (not shown) and the reference electrode is connected to the other terminal of the voltmeter; the potential difference between the two electrodes is a measure of the pH of the solution in which the combination electrode is immersed.

The measuring electrode 12 is filled with a solution 24 (measuring electrode filling solution) that establishes electrical conductivity with the conductive electrode 20. One well-known filling solution is the Ross® filling solution, an iodide/triiodide solution that is highly stable and operable over a wide temperature range. However, this solution is corrosive to many materials, and thus does not readily accommodate immersion of a temperature-measuring element in it.

The outer electrode 14 has the form of an elongated tube 26. The inner electrode is held within this tube by means of a lower bung 28 and an upper bung 30. These bungs are advantageously made of a plastic material, e.g., a silicon rubber, and are retained in position by compression against the tube wall 26. Additionally, they may be secured in place adhesively or by other means. A collar 32 (formed, e.g., of silicon rubber tubing) is snugly secured about the tube 16 and holds the lower bung 28 in place.

A reference electrode filling solution 36 is contained between the lower and upper bungs, 28 and 30, respectively. The filling solution 36 contacts the solution being analyzed through a ceramic junction 38, and provides an electrically conductive path between the solution being analyzed and an inner reference electrode 40 comprising an inner conductive electrode 42, an inner junction 44, and inner reference filling solution 46. A resealable filling port 48 enables replenishment of the filling solution 36 as necessary.

Bung 28 forms a chamber 50 of limited volume that is isolated from the main mass of filling solution 36 that is contained between bungs 28 and 30 and which is of substantially greater size. A notch 28a in the bung accommodates the ceramic junction 38 and provides clearance for the flow of filling solution 36 through the junction. This enables the junction 38 to be positioned lower on the electrode than would otherwise be the case.

The chamber 50 is filled with a liquid of good thermal conductivity which is advantageously, but not necessarily, the same as that of the filling solution 36. The chamber surrounds the lower portion of the stem 16 of the measuring electrode 12, and thus its temperature will closely track the temperature of the internal filling solution in the vicinity of the bulbous head 18 so as to ensure accurate temperature measurements when the electrode is immersed in an analyte. The reduced thermal mass of the chamber in which the temperature-measuring element is located shortens the response time, i.e., the time to reach temperature equilibrium between the measuring filling solution 24 in the inner (measuring) electrode 12 and the solution in the chamber 50 in which the thermistor is located.

Tubing 52, preferably of heat-shrinkable fluorinated ethylene propylene or Teflon®, extends downwardly through channels or ports in the bungs 30 and 28 into the chamber 50;

loops around the tubular stem 16; and then returns upwardly through further channels or ports in the bungs 28 and 30.

Figure 2A:
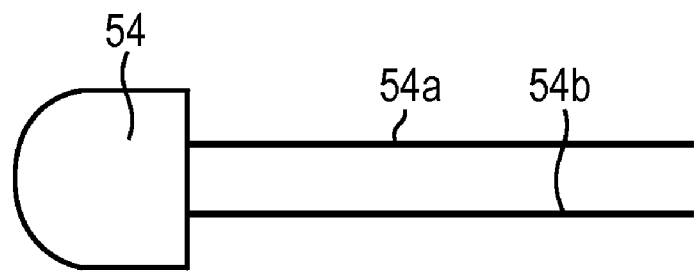
FIG. 2A is a side view of a thermistor showing lead wires extending from it.

FIG. 2A shows the temperature-measuring element in more detail. A thermistor head 54 has electrical leads 54a, 54b extending from it. These leads carry signals from the head 54 to measuring equipment (not shown) to which the electrode 10 is connected.

Figure 2B:
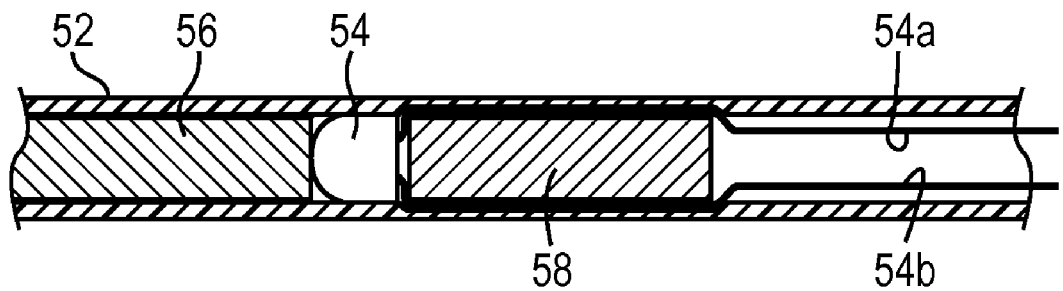
FIG. 2B is a sectional view of the thermistor of FIG. 2A enclosed within a thin-walled tube and abutted on both sides by short strands.

As may be seen in more detail in FIG. 2B, the thermistor head is snugly enclosed within the tubing 52. A first elongated strand 56 is butted against one end of the thermistor head 54; a second elongated strand 58 is butted against the other end of the thermistor head. The diameter of the elements 56, 58 is preferably approximately the same as that of the inner diameter of the tubing 52 so that the cross-sectional area of these elements is approximately the same as that of the inner channel of the tubing. This minimizes the presence of air in the tubing in the immediate vicinity of the thermistor head and thus enhances the rate of heat transfer between the head and the solution 50 surrounding it.

Also as shown in FIG. 2B, strand 58, when it is butted up against thermistor head 54, spreads the thermistor lead wires 54a, 54b against, and even into, the inner wall of flexible tubing 52 along that portion of the tubing in which the strand is located. This further enhances the rate of heat transfer between the lead wires, and thus the thermistor head to which they are attached, and the solution 50 surrounding them. Thus, the temperature-response time is further reduced. Beyond the strand 58 (i.e., to the right in FIG. 2B), the thermistor wires 54a, 54b are unconstrained by strand 58 and are able to extend more centrally within the tubing 52 away from its interior wall. Thus, as the tubing passes upwardly within reference electrode 14 and out of the temperature-measurement chamber as shown in FIG. 1, the rate of heat transfer between these wires and the surrounding environment, specifically, the reference filling solution 36 in the main reference chamber, is diminished, thus limiting a source of potential error in the temperature measurement.

As noted above, the strands 56, 58 may themselves be formed of thermally-conductive material, preferably of metal and advantageously of aluminum magnet wire. This material is commonly available in small-diameter sizes well suited to the present invention, has good thermal conductivity, and possesses a flexibility that greatly facilitates fabrication of the electrode.

As an example, in one embodiment of the invention, a 30K thermistor, together with a first strand 58 in the form of an aluminum magnet wire of approximately 0.5 inch length, were slid into one end of a fluorinated ethylene propylene (FEP) tube 50 of diameter slightly greater than that of the thermistor and of the heat sink. Care was taken to ensure that the two leads of the thermistor were extended along the inside wall of the tube during insertion so as to allow co-insertion of the element 58. A further strand of aluminum magnet wire of approximately 1.0 inch length was inserted into the other end of the tube and abutted against the thermistor. The tubing was then subjected to heat at an elevated temperature for a period of time in order to shrink it snugly around the thermistor 54 and the strands 56, 58, and thus hold them in place.

A circular loop of one and one-half turns was then formed in an intermediate portion of the tubing 50. The loop section included the thermistor and its surrounding positioning elements. The two ends of the tubing were then extended through ports or channels in the bung 28 and then the bung 30, which firmly hold them in place. The inner electrode 12 was then inserted into the reference electrode and sealed to it.

From the foregoing, it will be seen that we have provided improved temperature-compensation for ion-selective electrodes, particularly, but not limited to, combination electrodes. The construction is relatively simple and thus inexpensive to implement and is especially useful as applied to combination electrodes containing a corrosive solution which may otherwise damage temperature-measuring elements immersed in them.

It will be understood we have illustrated and described one preferred embodiment of the invention, and that that various changes may be made in the foregoing without departing from either the spirit or the scope of the invention which is described in the claims appended hereto.

What is claimed is:

1. In an ion-selective electrode having a measuring electrode including a first chamber having a sensing membrane at one end thereof for holding a measuring filling solution for measuring the concentration of an analyte ion and having a reference electrode including a second chamber for holding a reference solution for providing a reference potential for the measurement, said reference electrode being positioned adjacent said measuring electrode, the improvement comprising
a third chamber formed in said reference electrode adjacent said membrane for holding a thermally conductive liquid therein, said third chamber thermally insulated from said second chamber, in heat-transfer relation with the measuring electrode filling solution, and of substantially reduced volume with respect to said second chamber for containing a small thermal mass so as to closely track the temperature of measuring filling solution in the vicinity of the membrane, and of substantially reduced volume with respect to said second chamber; and
a temperature-sensing element in said third chamber.

2. An ion-selective electrode according to claim 1 in which said third chamber has a volume less that 10% of the volume of said first chamber.

3. An ion-selective electrode according to claim 2 in which said third chamber has a volume less that 5% of the volume of said first chamber.

4. An ion-selective electrode according to claim 1 in which said third chamber is formed from said second chamber by an insulating partition interposed between said second and third chambers.

5. An ion-selective electrode according to claim 1 in which said temperature-sensing element comprises a thermistor having electrical leads extending from an end thereof and enclosed within a thin-walled flexible plastic tubing.

6. An ion-selective electrode according to claim 5 which includes at least a first flexible strand butted against an end of said thermistor and forcing said leads against the inner wall of said tubing to thereby enhance heat transfer between said leads and the environment surrounding them.

7. An ion-selective electrode according to claim 6 in which said strand comprises a metallic wire.

8. An ion-selective electrode according to claim 7 in which said strand comprises aluminum magnet wire.

9. An ion-selective electrode according to claim 8 in which said tubing comprises heat-shrinkable fluorinated ethylene propylene material.

10. An ion-selective electrode according to claim 1 in which said third chamber extends around said first chamber.

11. An ion-selective electrode according to claim 10 in which said temperature-sensing element comprises a thermistor having electrical leads extending from an end thereof and enclosed within a thin-walled flexible plastic tubing, and which includes at least a first flexible strand butted against an end of said thermistor and forcing said leads against the inner wall of said tubing to thereby enhance heat transfer between said leads and the environment surrounding them.

12. In an ion-selective electrode having a measuring electrode including a first chamber having a sensing membrane at one end thereof for holding a measuring filling solution for measuring the concentration of an analyte ion and having a reference electrode including a second chamber for holding a reference solution for providing a reference potential for the measurement, said reference electrode substantially surrounding said measuring electrode, the improvement comprising:

a thermally insulating partition in said reference electrode dividing said second chamber into a first chamber segment for holding said reference solution and a second chamber segments of substantially smaller volume than said first chamber segment for holding a thermally conductive liquid of small thermal mass therein and positioned adjacent said membrane so as to closely track the temperature of said measuring filling solution in the vicinity of said membrane; and a temperature-sensing element in said second chamber segment for immersion in said thermal mass.

13. An ion-selective electrode according to claim 12 in which said thermal mass comprises first and second mass elements abutting said temperature-sensing element at opposed ends thereof.

14. An ion-selective electrode according to claim 13 in which said temperature-sensing element and said thermal mass are enclosed within a protective tubing.

15. An ion-selective electrode according to claim 14 in which said tubing comprises heat-shrinkable fluorinated ethylene propylene material.

16. An ion-selective electrode according to claim 14 in which said thermal mass is formed from aluminum magnet wire.

* * * * *

UNITED STATES PATENT AND TRADEMARK OFFICE
CERTIFICATE OF CORRECTION

| | | |
|---|---|---|
| PATENT NO. | : 8,287,705 B2 | Page 1 of 1 |
| APPLICATION NO. | : 12/692740 | |
| DATED | : October 16, 2012 | |
| INVENTOR(S) | : Moshe Hirshberg et al. | |

It is certified that error appears in the above-identified patent and that said Letters Patent is hereby corrected as shown below:

Col. 2, line 10 should read: "inner measuring ~~is~~ electrode surrounded by an outer reference"

Col. 3, line 8 should read: "lead wires is ~~is~~ significantly reduced. Accordingly, when the"

Col. 3, line 38 should read: "mistor is placed ~~is~~ within the tubing, that portion of the tubing"

Col. 3, line 67 should read: "illustrated and described ~~is~~ in the context of a combination"

Col. 7, line 13 should read: "chamber ~~segments~~segment of substantially smaller volume than"

Signed and Sealed this
Fifteenth Day of January, 2013

David J. Kappos
*Director of the United States Patent and Trademark Office*